United States Patent
Yuichi et al.

(10) Patent No.: US 6,841,705 B2
(45) Date of Patent: Jan. 11, 2005

(54) METHOD OF PRODUCING DIFLUOROMETHANE

(75) Inventors: Iikubo Yuichi, West Lafayette, IN (US); Hae Seok Ji, Ulsan (KR); Ook Jae Cho, Ulsan (KR)

(73) Assignee: Ulsan Chemical Co., Ltd., Ulsan (KR)

( * ) Notice: Subject to any disclaimer, the term of this patent is extended or adjusted under 35 U.S.C. 154(b) by 0 days.

(21) Appl. No.: 10/372,430

(22) Filed: Feb. 24, 2003

(65) Prior Publication Data

US 2004/0102659 A1 May 27, 2004

(30) Foreign Application Priority Data

Nov. 21, 2002 (KR) .............................. 10-2002-0072666

(51) Int. Cl.$^7$ .............................................. C07C 17/00
(52) U.S. Cl. ........................ 570/167; 570/165; 570/166; 570/168; 570/169; 570/170
(58) Field of Search .................. 570/167, 165, 570/166, 168, 169, 170

(56) References Cited

U.S. PATENT DOCUMENTS

| | | | | |
|---|---|---|---|---|
| 5,495,057 A | * | 2/1996 | Nam et al. ................... | 570/167 |
| 5,763,708 A | * | 6/1998 | Clemmer et al. ........... | 570/169 |
| 6,365,580 B1 | * | 4/2002 | Clemmer et al. ........... | 514/134 |

* cited by examiner

*Primary Examiner*—Elvis O. Price
(74) *Attorney, Agent, or Firm*—Harrison & Egbert

(57) ABSTRACT

A method of producing difluoromethane (HFC-32), which includes firstly reacting methylene chloride with hydrogen fluoride in gas phase at 280 to 340° C. in the presence of a fluorination catalyst to produce chlorofluoro methane, and secondly reacting the chlorofluoro methane with hydrogen fluoride in liquid phase at 60 to 80° C. in the presence of an antimony chloride catalyst. The method is advantageous in that HFC-32 is produced in high yield under mild reaction conditions using a relatively small amount of energy.

6 Claims, 1 Drawing Sheet

METHOD OF PRODUCING DIFLUOROMETHANE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention pertains to a method of producing difluoromethane.

BACKGROUND OF THE INVENTION

As well known to those skilled in the art, chlorofluorocarbon-based compounds conventionally used as foaming agents, abluents, aerosol propellants, and coolants, are known as materials with high ozone-depleting potential which destroy the ozone layer in the stratosphere, and so have been replaced with hydrochlorofluorocarbon (hereinafter, referred to sometimes as "HCFC"). However, recently, HCFC based materials are prone to be replaced with hydrofluorocarbon (hereinafter, referred to sometimes as "HFC") compounds, without ozone-depleting potential, because HCFC-based materials still have ozone depleting potential, even though its value is low.

Difluoromethane ($CH_2F_2$, hereinafter referred to sometimes as "HFC-32") is a substance used to replace chlorodifluoromethane ($CHF_2Cl$, hereinafter referred to sometimes as "HCFC-22"). Conventional methods of producing HFC-32 are classified into a liquid phase method and a gas phase method. According to the conventional gas phase method, methylene chloride ($CH_2Cl_2$, hereinafter referred to sometimes as "HCC-30") is reacted with hydrogen fluoride (HF) in gas phase at 350 to 500° C. in the presence of a fluorination catalyst to produce HFC-32. However, the conventional gas phase method is disadvantageous in that it is difficult to desirably control reaction conditions because of the high reaction temperature, side products are produced in great quantities to reduce yields of HFC-32, and complicated apparatuses are needed, thereby lowering reaction efficiency in comparison with the conventional liquid phase method.

As for the conventional liquid phase method, HCC-30 is reacted with hydrogen fluoride (HF) at 60 to 110° C. in the presence of an antimony pentachloride ($SbCl_5$) catalyst. However, this conventional liquid phase method is disadvantageous in that super acid is undesirably produced under high temperature and pressure to corrode a reactor made of metals, thus shortening the reactor's life span. Efforts to solve the above disadvantage have been made, in which a concentration of a catalyst is reduced or the reactor is made of a corrosion-resistant metal, but the above disadvantage was not completely solved. Therefore, a reactor, an inner wall of which is lined with fluorine resin (polytetrafluoroethylene, hereinafter referred to as "PTFE") is used to completely prevent corrosion of the reactor.

When HFC-32 is produced according to the conventional liquid phase method, it is necessary to continuously supply heat from an external heat source to a reactor so as to supply a reaction heat needed for the reaction. Hence, if the reactor lined with the PTFE resin and having a lower thermal conductivity than the metal reactor is used instead of the metal reactor, a separate heat supplying unit is additionally needed. In the case of the conventional gas phase method, super-heated hydrogen fluoride and HCC-30 in gas phase are fed into a reactor. However, these feeds are in a gas phase, so remaining in the reactor for a short time. Accordingly, super-heated feeds should be continuously and sufficiently fed into the reactor so as to maintain a desired temperature in the reactor. In other words, a great amount of super-heated unreacted feeds as well as feeds directly consumed in the gas phase reaction are needed so as to constantly maintain a reaction temperature. The unreacted feeds are separated from products by a heat exchanger, reheated, and fed into the reactor, thereby reducing energy efficiency.

Accordingly, there remains a need to develop a method of producing HFC-32 in high yield while securing energy savings.

BRIEF SUMMARY OF THE INVENTION

Therefore, it is an object of the present invention is to provide a method of producing HFC-32 in high yield under mild reaction conditions in which a relatively small quantity of energy is consumed.

The present inventors have conducted extensive studies into the method of producing HFC-32, keeping in mind a fact that a conventional gas phase method has disadvantages of large energy consumption due to a high reaction temperature and generation of great quantities of side products causing productivity to be reduced, and a conventional liquid phase method has disadvantages of severe corrosion of the reactor and low energy efficiency, resulting in the finding that HFC-32 is produced in high yield under mild reaction conditions using a relatively small amount of energy by catalytically reacting HCC-30 with HF in gas phase at a relatively low temperature of 340° C. or lower to produce chlorofluoro methane ($CH_2FCl$, hereinafter referred to as "HCFC-31"), and catalytically reacting chlorofluoro methane with HF in liquid phase at 60 to 100° C., thereby accomplishing the present invention. At this time, energy efficiency is improved because heat generated during a gas phase reaction is utilized in a liquid phase reaction.

BRIEF DESCRIPTION OF THE SEVERAL VIEWS OF THE DRAWINGS

The above and other objects, features and other advantages of the present invention will be more clearly understood from the following detailed description taken in conjunction with the accompanying drawings.

DETAILED DESCRIPTION OF THE INVENTION

Figure 1:
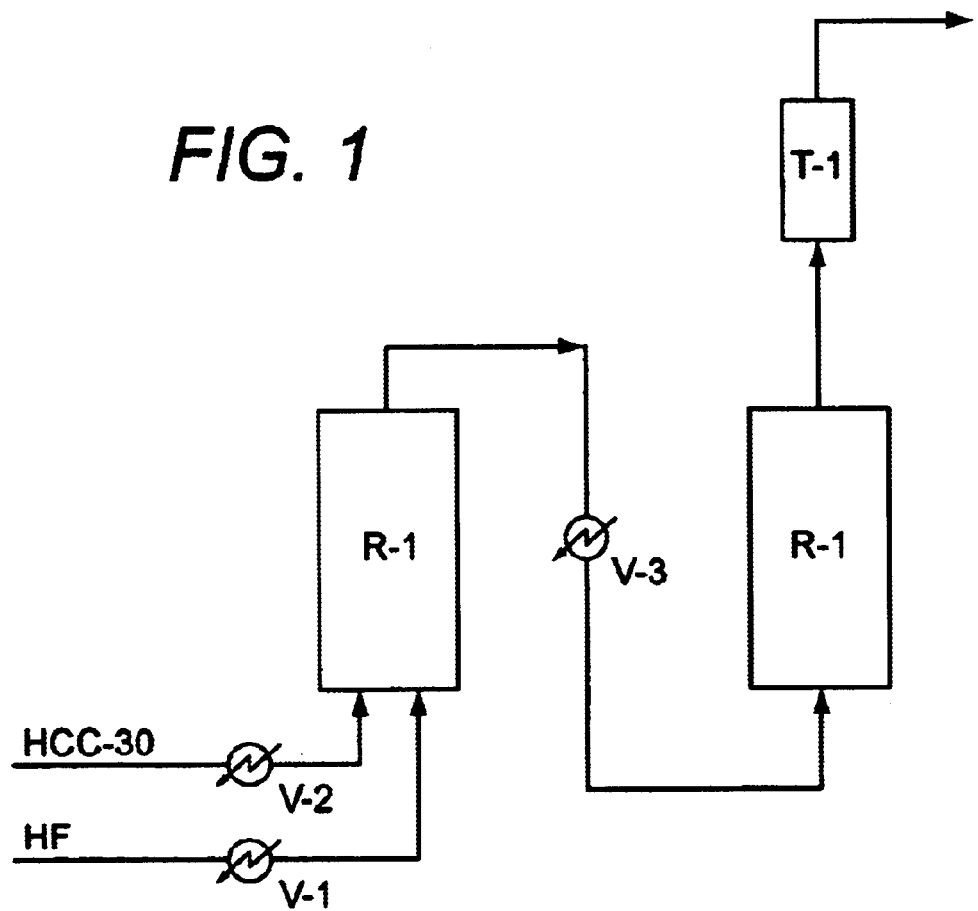
FIG. 1 is a flow diagram of a procedure of producing difluoromethane according to the present invention.

The present invention relates to a method of producing HFC-32 in high yield while securing high energy efficiency, in which HCC-30 is firstly reacted with HF in gas phase in the presence of a catalyst to produce a first product, and the first product is secondly reacted with hydrogen fluoride in liquid phase in the presence of another catalyst.

As described above, the present invention continuously conducts the gas-phase reaction and the liquid-phase reaction, thereby improving energy efficiency. In detail, HCC-30 is reacted with HF in gas phase in a first reactor R-1, and the first product mostly consisting of HCFC-31 is fed from a gas phase reactor R-1 into a liquid-phase second reactor R-2 lined with PTFE, and HCFC-31 and unreacted materials obtained from the gas-phase first reactor R-1 are fluorinated in liquid phase to produce HFC-32.

At this time, the liquid phase reaction utilizes heat generated during the gas phase reaction as reaction heat.

For convenience, the gas phase reaction is designated by a first process, and the liquid phase reaction is designated by a second process. As described above, the present invention utilizes a mixed method of the gas phase reaction and the liquid phase reaction methods. In detail, HCC-30 and HF are vaporized at 100 to 150° C., fed to the gas-phase first reactor at 280 to 340° C. in the first process to produce a product mostly comprising HCFC-31. HCFC-31 thus produced is fed in conjunction with HCC-30 and HF unreacted in the first reactor into the liquid-phase second reactor to produce HFC-32.

When HFC-32 is produced from HCC-30 by only a conventional gas-phase reaction, side products are produced in great quantities and reaction efficiency is low.

In the case of a conventional liquid-phase reaction, a reactor lined with resin is used so as to prevent corrosion of the reactor, but the reactor has poor thermal conductivity, so it is necessary to additionally feed raw material heated to a high temperature and not directly participating in the reaction into the reactor so as to supply heat required in the liquid phase reaction. This leaves a great quantity of unreacted reactants, and so a high efficiency heat exchanger is required and energy is consumed in the nearly same amount as the gas phase reaction.

According to the present invention, the gas phase and liquid phase reaction are continuously conducted. At this time, the gas phase reaction is performed at a lower temperature than the conventional gas phase reaction, heat generated from the gas phase reaction is utilized in the liquid phase reaction. Additionally, HCFC-31 is mostly produced in the gas phase reaction, and the first product obtained from the gas phase reaction is fluorinated during the liquid phase reaction to efficiently produce HFC-32.

A more detailed description of the gas and liquid phase reaction will be given, below.

First Process (Gas Phase Reaction)

HCC-30 and HF are heated so as to nearly reach a temperature required in the gas phase reaction and then fed into the gas phase reactor. In the conventional gas phase reaction, HFC-32 is produced at a relatively high temperature of 350 to 500° C. According to the present invention, however, the gas phase reaction is performed at a relatively low temperature of 280 to 340° C. to mostly produce HCFC-31, and a life span of a catalyst is extended because of a low reaction temperature. Furthermore, the conventional gas phase reaction is disadvantageous in that fluorination reaction of HCC-30 into HFC-32 through two steps is conducted at once, thus being poor in yield. On the other hand, the gas phase reaction according to the present invention performs a single step fluorination reaction of HCC-30 into HCFC-31 at a relatively low temperature, thus readily yielding HCFC-31 in high yield. Furthermore, in the gas phase reaction of the present invention, a fluorination catalyst is used, in which any one selected from the group consisting of chromium oxide ($Cr_2O_3$), chromium oxyfluoride (CrFO or $Cr_2F_2O_2$), aluminum fluoride ($AlF_3$), and aluminum chlorofluoride ($AlClF_2$ or $AlCl_2F$) is supported by carbon or alumina in an amount of about 5 to 10 wt %. These types of catalysts are well known in the art.

If a reactant, HCC-30, is fed in conjunction with a predetermined amount of oxygen to the gas phase reactor, activity of the catalyst is maintained for an extended period. In the case of the gas phase reaction of the present invention, HCFC-31 obtained from HCC-30 through the single step fluorination reaction is a main product, so the catalyst's life span is sufficiently prolonged by only adding 0.005 to 0.2% oxygen to the reactor. This concentration of oxygen is lower than that of the conventional gas phase reaction having an object of producing HFC-32. A reaction pressure in the first process is 8 to 12 $kg/cm^2G$ higher than that of the second process (liquid phase reaction), and HCFC-31, hydrogen chloride, a small amount of HFC-32, unreacted hydrogen fluoride, and HCC-30 are fed in gas phase into the second reactor. A high temperature product produced from the first reactor transfers its heat through a heat exchanger set between the first reactor and the second reactor into the second reactor to control a reaction temperature of the second process.

Second Process (Liquid Phase Reaction)

In the second process according to the present invention, hydrogen fluoride is reacted with HCFC-31 at 60 to 80° C. under 6 to 10 $kg/cm^2G$ in the presence of an antimony catalyst, and a reactor lined with PTFE resin on an inner wall thereof is used so as to prevent corrosion of the reactor. However, it is difficult to supply sufficient heat required in the liquid phase reaction by using only heat supplied through a jacket on an outer wall of the second reactor because the reactor lined with the PTFE resin has low thermal conductivity. Therefore, additional heat of gas produced from the first process is used as a reaction heat of the second reactor, and the second process is performed without additional heating devices. In particular, in the second process, HCFC-31 is reacted with hydrogen fluoride in the presence of the antimony catalyst according to the single step fluorination reaction to mostly produce HFC-32, thus reaction conditions of the second process are mild and conversion yield of HCFC-31 into HFC-32 is high in comparison with the conventional liquid phase reaction in which HCC-30 is converted into HFC-32 according to the two step fluorination reaction.

In the case of the conventional liquid phase reaction using the antimony catalyst ($SbCl_xF_y$, wherein x+y=5, $1 \leq y \leq 5$), when activity of the antimony catalyst is reduced from Sb(+5) to Sb(+3), the activity is recovered to Sb(+5) by continuously or intermittently adding $Cl_2$ to the second reactor. On the other hand, in the case of the second liquid phase reaction of the present invention, an activity reduction rate [Sb(+3)] of the catalyst is relatively slow because HCFC-31 is converted into HFC-32 according to the single step fluorination reaction. Accordingly, the present invention is advantageous in that a relatively small amount of chloride is used in comparison with the conventional liquid phase reaction With reference to FIG. 1, a flow diagram of a procedure of producing difluoromethane according to the present invention is illustrated.

In the first process, raw materials, that is to say HCC-30 and HF, are heated to 80 to 150° C. by vaporizers V-1 and V-2, and then fed into the first reactor R-1. At this time, a chromium oxide catalyst is packed in the first reactor R-1, the first reactor is heated to 280 to 340° C., and 2 to 10 moles hydrogen fluoride per unit mole HCC-30 is fed into the first reactor. A temperature of a first product obtained from the first reactor R-1 is controlled by a heat exchanger V-3 so as to maintain a reaction temperature of a second reactor R-2 within a range of 60 to 100° C. At this time, pressure in the first reactor ranges from 8 to 12 kg/cm²G.

As for the second process, the liquid phase reactor R-2 is lined with a PTFE resin so as to prevent corrosion of the reactor, and antimony pentachloride (SbCl₅) is fluorinated with hydrogen fluoride to form a $SbCl_xF_y$ catalyst (x+y=5, $1 \leq y \leq 5$). Additionally, HCFC-31, hydrogen fluoride, hydrogen chloride, a small amount of unreacted HCC-30, and a small amount of HFC-32 are fed from the first reactor to a lower part of the second reactor R-2. The second liquid phase reaction is performed at 60 to 80° C. under pressure of 6 to 10 kg/cm²G to produce HFC-32. HFC-32 thus produced is moved through a separate column T-1 positioned at an upper part of the second reactor to a refinery.

A better understanding of the present invention may be obtained in light of the following examples which are set forth to illustrate, but are not to be construed to limit the present invention.

EXAMPLE

Gas Phase Reaction 1.2 kg of alumina catalyst in which 8 wt % chromium oxide was supported by alumina was stuffed in an Inconel pipe with volume of 3 L, thereby accomplishing a first reactor R-1. Vaporized hydrogen fluoride and nitrogen gas were fed into the first reactor R-1 heated to 300° C. to fluorinate the catalyst. HCC-30 and hydrogen fluoride were then fed into the first reactor. At this time, 2 to 10 moles hydrogen fluoride per unit mole HCC-30 was fed into the first reactor under 8 to 12 kg/cm²G for 15 to 20 sec. Products obtained from the first reactor were heat-exchanged and then used as raw material of a liquid phase reaction.

Liquid Phase Reaction

A SbCl₅ catalyst was stuffed into a 16 L second reactor lined with PTFE, resin, hydrogen fluoride was fed into the second reactor at 50° C. to fluorinate the SbCl₅ catalyst, and hydrogen fluoride (HF) was fed into the second reactor in such a way that a liquid level in the second reactor was maintained at 50%. Products obtained from the first reactor were fed into the second reactor at 60 to 80° C. under 6 to 10 kg/cm²G.

After being rinsed with water to remove acid components, products obtained from the gas and liquid phase reaction were respectively analyzed by a gas chromatography analyzer.

As a result, products obtained from the gas phase reaction consisted of 57 to 66% HFC-31, 14 to 34% HFC-32, and 7 to 25% HFC-30 products obtained from the liquid phase reaction consisted of 90 to 95% HFC-32, 3 to 8% HCFC-31, 0 to 4% HCC-30.

As described above, the present invention is advantageous in that HFC-32 is produced in high yield under mild reaction conditions using a relatively small amount of energy.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

We claim:

1. A method of producing difluoromethane, comprising:

firstly reacting methane chloride with hydrogen flouride and oxygen in gas phase at 280 to 340° C. in a presence of fluorination catalyst to produce chlorofluoro methane; and secondly reacting the chlorofluoro methane with hydrogen flouride in liquid phase at 60 to 80° C. in a presence of an antimony chloride catalyst.

2. The method according to claim 1, wherein the fluorination catalyst is selected from the group consisting of chromium oxide, chromium oxyfluoride aluminum fluoride, and aluminum chloroflouride.

3. The method according to claim 1, further comprising reacting 1 mol methylene chloride with 2 to 10 moles hydrogen flouride to produce the chlorofluoro methane.

4. The method according to claim 1, wherein the firstly reacting is preferred under 8 to 12 kg/cm²G and the secondly reacting is preformed under 6 to 10 kg/cm²G.

5. The method according to claim 1, wherein the firstly reacting is preformed for 15 to 20 sec.

6. The method according to claim 1, wherein the firstly reacting is performed in an oxygen concentration of 0.005 to 2%.

* * * * *